United States Patent
Zondervan (10) Patent No.: US 9,642,429 B2
(45) Date of Patent: May 9, 2017

(54) STERILE CASE FOR ELECTRONIC DEVICES USED IN MEDICAL PROCEDURES

(71) Applicant: SteriDev, LLC, Lansing, MI (US)

(72) Inventor: Robert L. Zondervan, Lansing, MI (US)

(73) Assignee: STERIDEV, LLC, Lansing, MI (US)

( * ) Notice: Subject to any disclaimer, the term of this patent is extended or adjusted under 35 U.S.C. 154(b) by 0 days.

(21) Appl. No.: 14/854,339

(22) Filed: Sep. 15, 2015

(65) Prior Publication Data

US 2017/0035166 A1 Feb. 9, 2017

Related U.S. Application Data

(60) Provisional application No. 62/200,835, filed on Aug. 4, 2015.

(51) Int. Cl.
*A45C 11/00* (2006.01)
*A45C 13/00* (2006.01)
(Continued)

(52) U.S. Cl.
CPC ............. *A45C 11/00* (2013.01); *A45C 13/005* (2013.01); *A45F 5/00* (2013.01); *A61B 46/10* (2016.02);
(Continued)

(58) Field of Classification Search
CPC .............. A45C 11/00; A45C 2011/003; A45C 2011/002; A61B 46/10; A61B 50/31; A61B 2050/311
(Continued)

(56) References Cited

U.S. PATENT DOCUMENTS 3,832,738 A   9/1974 Kliemann
4,761,379 A * 8/1988 Williams ........... A61B 10/0051
                                                      206/569

(Continued)

FOREIGN PATENT DOCUMENTS

GB          2500943 A    10/2013
WO     WO2014012013 A1    1/2014

OTHER PUBLICATIONS

EP Search Report for EP Application No. 16182084.0 dated Oct. 20, 2016, 8 pages.

(Continued)

*Primary Examiner* — Steven A. Reynolds
(74) *Attorney, Agent, or Firm* — Reising Ethington P.C.; Jeffrey L. Doyle (57) ABSTRACT

A sterile case for an electronic device used during medical procedures includes a rigid housing with at least one transparent face. An opening in the housing permits movement of the device into and out of the housing in, for example, a direction parallel to the length or width of the housing. A door attached to the housing moves between open and closed positions to seal the opening. A sleeve is configured to be received, when the door is in the open position, partially within the housing and to extend outward from the housing through the opening. The sleeve defines a bore aligned with the opening and configured to receive the device and to permit insertion of the device through the sleeve into the housing without contact between the device and a rim of the housing surrounding the opening.

33 Claims, 5 Drawing Sheets (51) Int. Cl.
    *A45F 5/00* (2006.01)
    *A61B 50/31* (2016.01)
    *A61B 46/10* (2016.01)
    *A61B 50/00* (2016.01)

(52) U.S. Cl.
    CPC ........ *A61B 50/31* (2016.02); *A45C 2011/002* (2013.01); *A45C 2011/003* (2013.01); *A61B 2050/005* (2016.02); *A61B 2050/0056* (2016.02); *A61B 2050/0066* (2016.02); *A61B 2050/0067* (2016.02)

(58) Field of Classification Search
    USPC .................................................. 206/320, 305
    See application file for complete search history.

(56) References Cited

U.S. PATENT DOCUMENTS

| | | | | |
|---|---|---|---|---|
| 5,187,850 | A * | 2/1993 | McCammon | A61M 5/3205 206/366 |
| 5,577,610 | A * | 11/1996 | Okuda | G03F 1/62 206/316.1 |
| 6,680,027 | B2 | 1/2004 | Kang et al. | |
| 6,799,695 | B1 * | 10/2004 | Borrero | A47K 10/427 206/467 |
| 7,118,559 | B2 | 10/2006 | Toomey | |
| 7,705,559 | B2 | 4/2010 | Powell et al. | |
| 8,550,714 | B2 * | 10/2013 | Ben-Shushan | A45C 1/02 24/30.5 R |
| 8,867,198 | B2 * | 10/2014 | Steele | A45C 11/00 206/320 |
| 2003/0111366 | A1 * | 6/2003 | Enners | G06F 1/1626 206/305 |
| 2003/0149424 | A1 | 8/2003 | Barlev et al. | |
| 2005/0116003 | A1 * | 6/2005 | Butler | A45C 11/22 224/604 |
| 2007/0166188 | A1 * | 7/2007 | Ryterski | A61B 19/081 422/40 |
| 2007/0261978 | A1 * | 11/2007 | Sanderson | A45C 11/22 206/320 |
| 2012/0000804 | A1 | 1/2012 | Barnes et al. | |
| 2012/0124943 | A1 | 5/2012 | Nakamura et al. | |
| 2012/0174373 | A1 | 7/2012 | Whitney et al. | |
| 2013/0064478 | A1 | 3/2013 | Sold et al. | |
| 2014/0224685 | A1 * | 8/2014 | Carnevali | G06F 1/1626 206/320 |
| 2014/0270583 | A1 | 9/2014 | Anderson | |

OTHER PUBLICATIONS

Otter Box; iPhone 6 Plus, Defender Series Case; 10 pages, accessed May 11, 2015.
Whitney Medical Solutions; eShield Covers; http://whitneymedicalsolutions.com/eshield-covers, 2 pages, accessed May 11, 2015.
LifeProof iPhone, iPad, and Samsung Galaxy Cases / LifeProof; http://www.lifeproof.com/en/, 8 pages, accessed May 11, 2015.

* cited by examiner

STERILE CASE FOR ELECTRONIC DEVICES USED IN MEDICAL PROCEDURES

CROSS REFERENCE TO RELATED APPLICATIONS

This application claims the benefit of U.S. Provisional Patent Application Ser. No. 62/200,835 filed Aug. 4, 2015, which is incorporated herein by reference in its entirety.

TECHNICAL FIELD

This invention relates generally to the use of electronic devices in sterile medical environments, and more specifically, but not exclusively, to a sterile case configured to accept and house an electronic device (e.g., a non-sterile, portable electronic device) in order to permit use of the device in a sterile medical environment.

BACKGROUND

Surgical and other medical procedures must be performed in sterile environments (i.e., environments that are free or at least substantially free from biological contaminants including bacteria, fungi and viruses) to reduce the risk of infection in patients undergoing medical procedures. As a result, great care is taken to maintain sterility and prevent contamination of the environment from people or objects brought into the sterile medical environment.

In recent years, there has been a significant increase in demand to be able to bring electronic devices into sterile medical environments. Surgeons and other medical practitioners use electronic devices, for example, mobile or portable electronic devices, to capture and share media from medical procedures and complex pathology and to access software applications useful during procedures. Images of pathology, surgical instruments, techniques, etc., and related medical procedures (whether still images or video) are useful for educating other surgeons, residents and medical students through, for example, medical journals, lectures, and webcasts. The images are also useful for consulting with other medical practitioners regarding treatment and for documenting treatment. Software applications can be used, for example, to fuse live images with superimposed graphics to aid in placement and guidance of medical devices among other tasks. Many medical software applications, however, require that the device on which they are installed be in close proximity to the procedure that is being performed. Because of the usefulness of electronic devices during medical procedures, a risk exists that surgeons or other medical practitioners will attempt to bring non-sterile devices into or around sterile environments and use those devices, thereby increasing the risk of infection to patients.

The inventors herein have recognized a need for a sterile case for an electronic device that will overcome one or more of the above-identified deficiencies.

SUMMARY

According to one embodiment, there is provided a sterile case for an electronic device. The sterile case includes a rigid housing having at least one face that is transparent and has an opening configured to permit movement of the device into and out of the housing. The housing also defines a rim about the opening. The case further includes a door attached to the housing and configured to move between a closed position in which the door closes the opening in the housing and an open position in which the door is distant from the opening in the housing. The case further includes a sleeve configured to be received, when the door is in the open position, partially within the housing and to extend outward from the housing through the opening. The sleeve defines a bore aligned with the opening of the housing and configured to receive the device and to permit and guide insertion of the device through the sleeve into the housing without contact between the device and the rim of the housing. The sleeve may also be removable in the sense that it may be removed from the housing following the insertion of the device into the housing, and may also be disposable in that it may be disposed of after one or a predetermined number of uses.

According to another embodiment, there is provided sterile case for an electronic device. The sterile case includes a rigid housing having at least one face that is transparent and has an opening configured to permit movement of the device into and out of the housing. The housing also defines a rim about the opening, and includes an attachment element for attaching the housing to another structure. The sterile case further includes a door attached to the housing and configured to move between a closed position in which the door closes the opening in the housing, and an open position in which the door is distant from the opening in the housing. The case still further comprises a sleeve configured to be received, when the door is in the open position, partially within the housing and to extend outward from the housing through the opening, the sleeve defining a bore aligned with the opening and configured to receive the device and to permit and guide insertion of the device through the sleeve and into the housing without contact between the device and the rim of the housing.

According to yet another embodiment, there is provided a sterile case for an electronic device. The sterile case includes a rigid housing having a length and a width. The housing has a first face that is transparent and electroconductive, a second face defining a transparent window configured for alignment with a camera lens of the electronic device, and an opening configured to permit movement of the device into and out of the housing in a direction parallel to one of the length and the width, the housing further defining a rim about the opening. The sterile case further includes a door attached to the housing by a hinge and configured to move between a closed position in which the door closes the opening in the housing and an open position in which the door is distant from the opening in the housing. The case still further includes a latch to secure the door to the housing when the door is in the closed position. The case yet still further includes a sleeve configured to be received, when the door is in the open position, partially within the housing and to extend outward from the housing through the opening, the sleeve defining a bore aligned with the opening of the housing and configured to receive the device and to permit and guide insertion of the device through the sleeve and into the housing without contact between the device and the rim of the housing. The case further includes a seal formed on the rim of the housing or the door of the case.

The foregoing and other aspects, features, details, utilities, and advantages of the present invention will be apparent from reading the following description and claims, and from reviewing the accompanying drawings.

BRIEF DESCRIPTION OF THE DRAWINGS

One or more embodiments of the invention will hereinafter be described in conjunction with the appended drawings, wherein like designations denote like elements, and wherein.

DETAILED DESCRIPTION

Referring now to the drawings wherein like reference numerals are used to identify identical components in the various views, FIGS. 1-7 illustrate one embodiment of a sterile case 20 for an electronic device to allow the device to be used by surgeons or other medical practitioners in a sterile environment during a medical procedure. The case 20 may find application with any number of electronic devices. For example, in several of the illustrated embodiments, the electronic device comprises a mobile communications device and, in particular, a cellular phone (or "smart phone"). It should be understood, however, that the mobile communications device may comprise any of a wide variety of devices such as, for example and without limitation, devices configured for wireless communication with a cellular or other telecommunications network through which the device may maintain communication with the network despite changes in location of the device including, for example, tablets, personal digital assistants ("PDAs"), or a laptop computers with wireless transceivers built in or connected thereto, to cite only a few examples. Electronic devices other than mobile communications devices that the case 20 may be configured for use with include, for example and without limitation, cameras for capturing still images, cameras for capturing video images, and other suitable devices, for example, other suitable portable and/or hand-held electronic devices. In any event, the case 20 includes a housing 22, a door 24, a hinge 26, a seal 28 and/or a seal 30, and a sleeve 32 that, in an embodiment, may be a disposable sleeve.

The housing 22 is provided to receive and contain the electronic device to prevent biological contaminants that may be present on the device from coming into contact with persons and objects in a sterile environment. The housing 22 is generally rigid and may be made from a variety of conventional polymer materials, including in an illustrative embodiment and without limitation, clarified polypropylene. The housing 22 may be formed (e.g., through molding or other conventional processes) as a unitary or one-piece body to eliminate joints and thereby reduce the risk that biological contaminants will escape the interior of the housing 22. In the illustrated embodiment, the housing 22 has a shape substantially in the form of a rectangular prism. As used herein, it should be understood that use of the phrase rectangular prism includes shapes that approximate a rectangular prism and therefore having a length l, a width w, and a height h. It will be appreciated, however, that in other embodiments, the housing may have a shape/form other than rectangular prism, as in at least some embodiments the shape of the housing 22 may be dependent on the shape of the electronic device it is configured to receive and may include features such as flanges, rounded corners, etc. intended to provide ergonomic or other benefits. Accordingly, the present disclosure is not intended to be limited to the housing 22 having any particular shape(s).

In at least the embodiment wherein the housing 22 has a shape in the form of a rectangular prism, the housing 22 includes two opposed faces 34, 36 defined by the length l and the width w and three faces 38, 40, 42 extending between the faces 34, 36 with the faces 38, 40 defined by the length l and height h and the face 42 defined by the width w and the height h. A portion or all of at least one face—face 34 in the illustrated embodiment—is transparent in order to permit a user to view and interact with typical touch screen displays on the electronic device. For similar reasons, all or at least one face—face 34 in the illustrated embodiment—may also be flexible and/or electroconductive and/or include flexible (or deformable) and/or electroconductive features. For example, in an instance where the face 34 is flexible, when a user presses an area of the face 34 that portion of the face 34 may contact the touch screen of the device to allow the user's selection/input to be received by the device. In any event, in an embodiment, the electroconductive face or features may be formed of polyethylene terephthalate or thermoplastic polyurethane, though other or additional suitable materials may certainly be used.

Another face—face 36 opposite face 34 in the illustrated embodiment—may define a transparent window 44 configured for alignment with a camera lens of a camera in the electronic device. It should be understood that the relative location of the window 44 may vary depending on the construction of the electronic device with which the case 20 will be used. All or at least one face—face 36 in the illustrated embodiment—may also include corporate logos or other indicia (represented as box 46 in FIGS. 1 and 3), ancillary tactile components (not shown) approximating the underlying device components (e.g., raised, functional "button" overlaying the device's actual volume control button, etc.), instructions for use (not shown), or other indicia formed in or attached to the face(s).

The housing 22 defines an opening 48 configured to permit movement of the electronic device into and out of the housing 22. The opening 48 may be formed in such a way that it permits insertion and removal of the device while also minimizing the size of the opening 48 and the size of any seal surrounding the opening 48. Accordingly, the opening 48 may be configured to permit movement of the device into and out of the housing 22 in a direction parallel to the length or width of the housing 22 (as opposed to, for example a clamshell structure or inserting the device through the sides 34 or 36). In the illustrated embodiment, the opening 48 is formed in a side of the housing 22 opposite the face 42 and defined by the width w and height h of the housing 22 such that the device is moved into and out of the housing 22 in the direction parallel to the length l of the housing 22. The side of the housing 22 in which the opening 48 is formed defines a rim 50 disposed about a portion or all of the opening 48.

The door 24 is provided to control access to the interior of the housing 22. The door 24 is attached to the housing 22 by the hinge 26 and is configured to move between a closed position in which the door 24 closes the opening 48 and an open position (shown in FIGS. 1-7) in which the door 24 is distant from the opening 48. The door 24 is sized to close the opening 48 and engage the rim 50 when the door 24 is in the closed position.

The hinge 26 is provided to attach the door 24 to the housing 22 and to allow movement of the door 24 between the open and closed positions. The hinge 26 may comprise a pin extending between interleaved rings formed in or mounted on the housing 22 and the door 24; though other suitable hinges or hinge configurations may certainly be used instead (e.g., a living hinge). The hinge 26 enables rotation of the door 24 about an axis 52 between a closed position and an open position. The hinge 26 may be a spring loaded hinge biasing the door 24 to a closed position in order to reduce the chance that the door 24 will inadvertently open after insertion of the electronic device and contaminate the sterile field. It should be understood, however, that various latch and/or other features (not shown) may alternatively be formed in or mounted to the housing 22 and/or the door 24 to enable the door 24 to be locked in a closed position.

The seals 28, 30 are provided to reduce the risk of biological contaminants escaping from the interior of the housing 22 after insertion of an electronic device. The seals 28, 30 may be disposed along the rim 50 and/or on a surface of the door 24 facing the rim 50. The seals 28, 30 may, in an embodiment, be configured to engage one another. In another other embodiment, the seals 28, 30 may not engage one another but rather seal 28 may engage a surface of the door 24 and the seal 30 may engage a surface of the housing 22. A variety of conventional seals may be employed including labyrinth seals defining a tortuous path for any contaminants to escape the interior of the housing 22, gaskets, etc. While the description above has been with respect to an embodiment wherein the case 20 includes a pair of seals 28, 30, it will be appreciated that in other embodiments, the case 20 may include only one seal (e.g., either seal 28 or seal 30) or may include more than two seals. Accordingly, the present disclosure is not intended to be limited to any particular number of seals.

The sleeve 32 is provided to reduce the risk of contamination of exterior surfaces of the housing 22 during insertion or transfer of the electronic device into the case 20. The sleeve 32 is configured such that a portion 54 of the sleeve 32 is received within and extends into the housing 22 (best shown in FIG. 7) when the door 24 is in the open position prior to insertion of the electronic device. The sleeve 32 is further configured to extend outward from the housing 22 through the opening 48 and includes a portion 56 that extends outward from the portion 54. The portion 56 may be configured to prevent insertion of the entirety of the sleeve 32 through the opening 48 and may therefore have dimensions that prohibit insertion of the portion 56 into the opening 48. In the illustrated embodiment the portion 56 is longer and wider than the portion 54 such that the portions 54, 56 define a shoulder at the intersection of the portions 54, 56 configured to engage the rim 50. When the sleeve 32 is inserted within the opening 48, the sleeve 32 prevents the door 24 from assuming the closed position until the sleeve 32 is removed. The portions 54 and 56 may form a unitary or one-piece body. The portions 54, 56 define a bore 58 that is aligned with the opening 48 when the sleeve 32 is inserted through the opening 48 and disposed within the housing 22, and the bore 58 is configured to receive the electronic device. In an embodiment, the sleeve 32 (or at least the bore 58 thereof) may have a generally funnel-like shape such that and the bore 58 may taper inwardly moving in a direction from a point furthest from the opening 48 towards the opening 48 in order to guide insertion and placement of the device into the housing 22. Because the bore 58 extends from one side of the rim 50 to the opposite of the rim 50, the sleeve 32 permits insertion of the electronic device through the sleeve 32 and the opening 48 in the housing 22 without any possibility of contacting the rim 50. As a result, any biological contaminants on the device cannot be transferred to the rim 50 and/or other exterior surfaces of the housing 22 during insertion of the device. In an embodiment, the case 20 may be packaged such that the sleeve 32 is pre-installed in or with the housing 22. In other embodiments, the sleeve 32 may not be pre-installed in or with the housing 22 but rather may have to be installed in or with the housing 22 before use of the case 20. In any event, the sleeve 32 may be "removable" in at least the sense that it may be removed from the housing 22 following the insertion of an electronic device therein.

Figure 1:
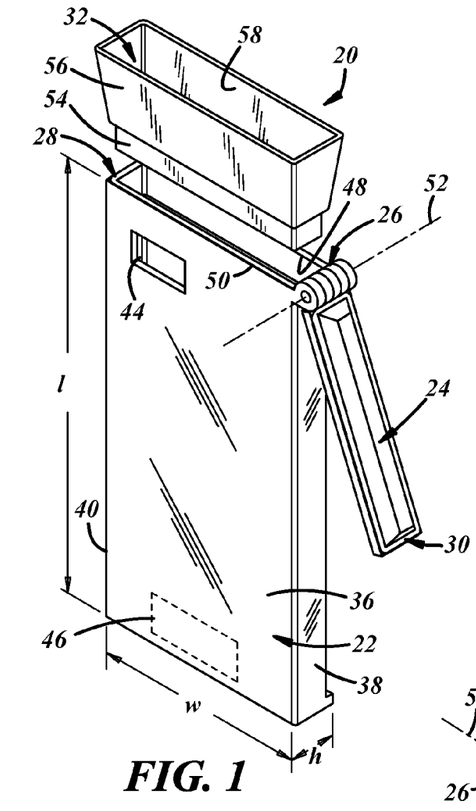
FIGS. 1 and 2 are perspective views of a sterile case in accordance with one embodiment of the present teachings.
Figure 2:
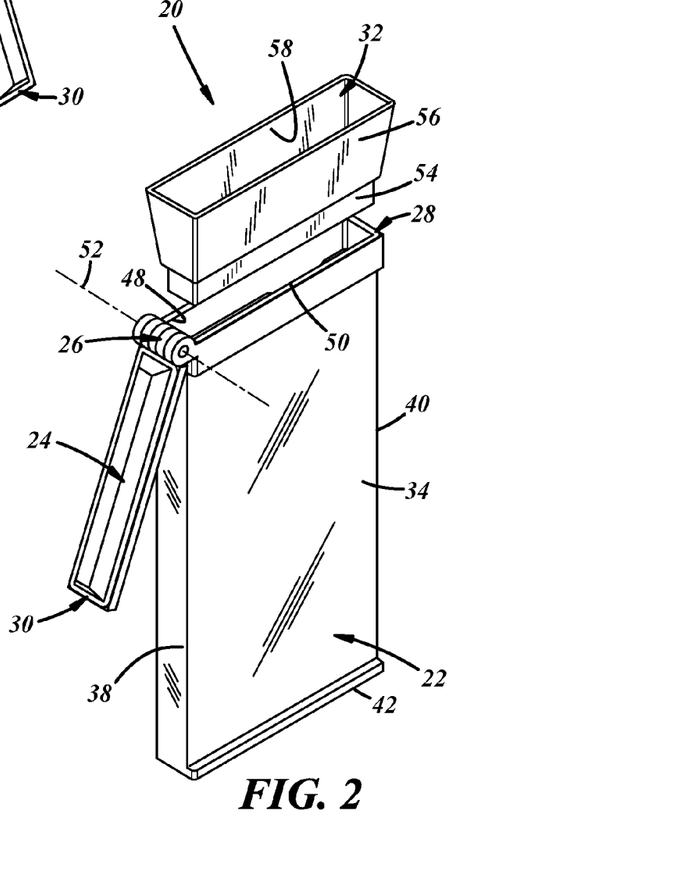
Figure 3:
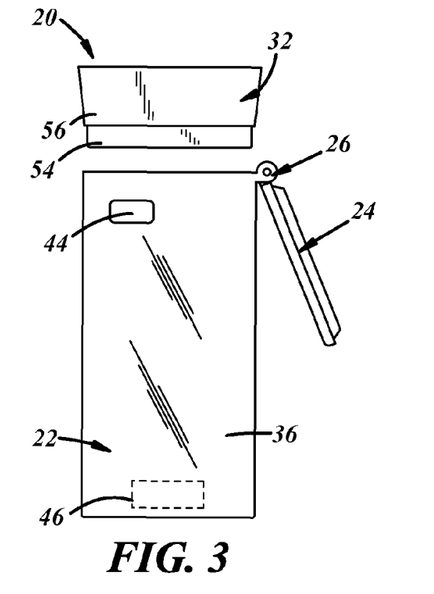
FIGS. 3-6 are side views of the sterile case illustrated in FIGS. 1 and 2.
Figure 4:
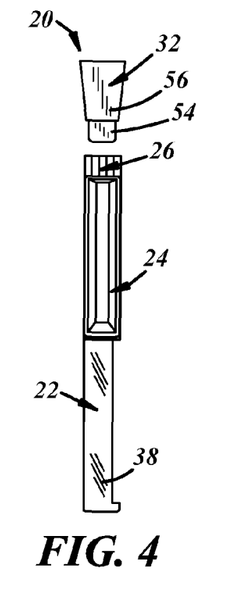
Figures 5, 6:
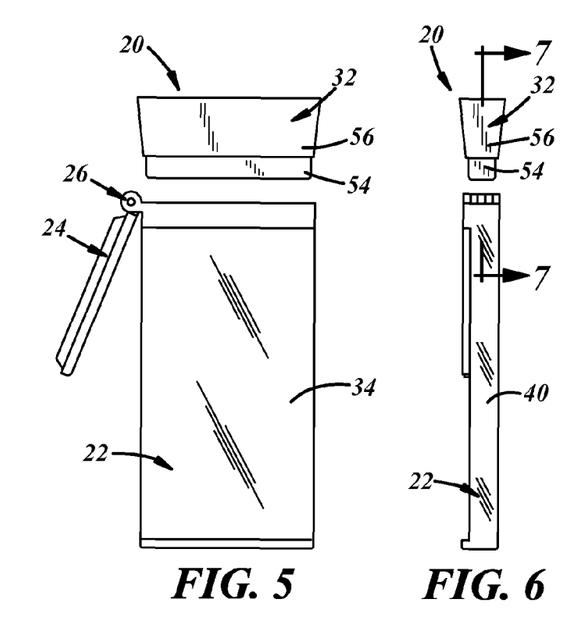
Figure 7:
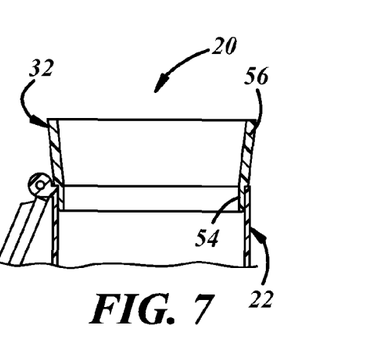
FIG. 7 is a cross section view of a portion of the sterile case illustrated in FIGS. 1-6 showing a sleeve of the case inserted into a housing of the case.
Figure 8:
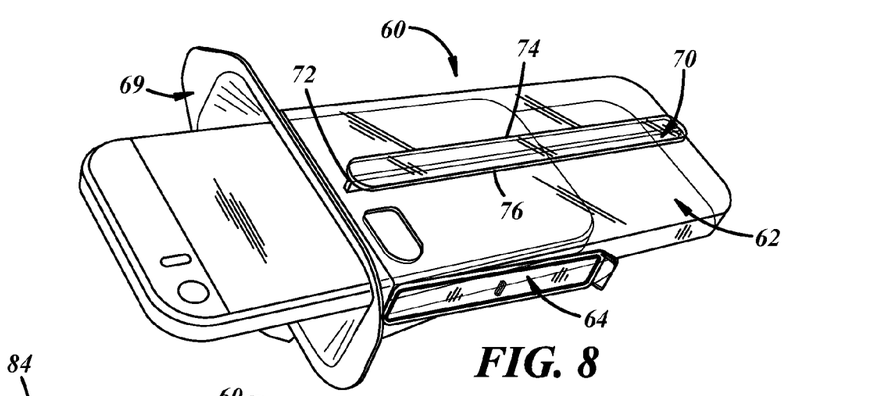
FIG. 8 is a perspective view of a sterile case in accordance with another embodiment of the present teachings in which an example electronic device has been partially inserted.
Figures 9, 10A:
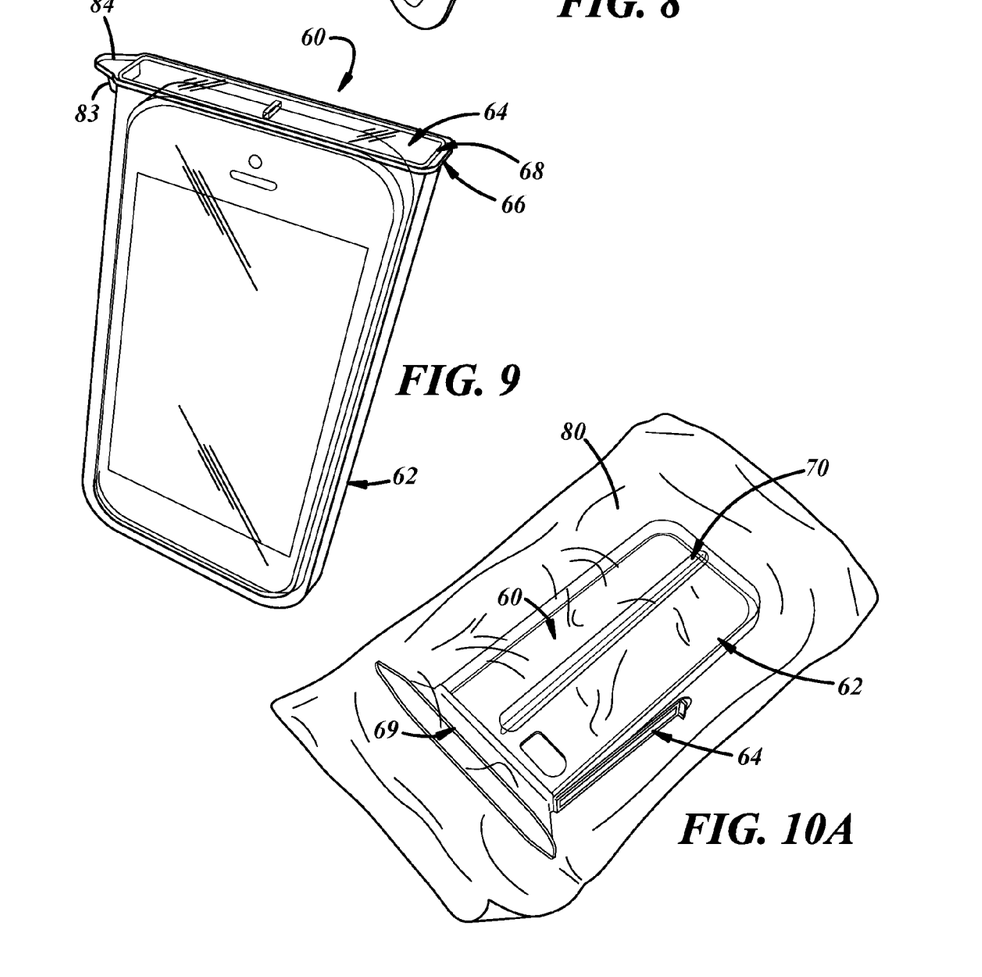
FIG. 9 is a perspective view of the sterile case of FIG. 8 after the electronic device has been fully inserted.
FIGS. 10A-10G illustrate steps in a method for using an electronic device in a sterile medical environment in accordance with embodiments of the present teachings.

Referring now to FIGS. 8 and 9, another embodiment of a sterile case 60 for an electronic device is illustrated that allows the device to be used by surgeons or other medical practitioners in a sterile environment during a medical procedure. The case 60 includes a housing 62, a door 64, a hinge 66, one or more seals, for example, seals 67, 68, and a sleeve 69 that, in an embodiment, may be disposable. Aside from differences in shape to accommodate manufacturing, ergonomic use and other concerns, the housing 62, the door 64, the hinge 66, the seals 67, 68, and the sleeve 69 are substantially similar to the housing 22, the door 24, the hinge 26, the seals 28, 30, and the sleeve 32 of case 20 described above and illustrated in FIGS. 1-7 in terms of structure and function, and reference may therefore be had to the description hereinabove.

The housing 62 does, however, differ from the housing 22 in that the housing 62 includes attachment means, such as an attachment element in the form of, for example, a rail 70, for attaching the housing 62 to another structure to, for example, securely position the electronic device within the sterile environment of the procedure. The rail 70 is formed on, or coupled to, an exterior surface of the housing 62 and may be formed on, or coupled to, one face of the housing 62. In the illustrated embodiment, the rail 70 is formed on a face of the housing 62 opposite the face configured to allow viewing and interaction with a touch screen of the electronic device. The rail 70 may be configured to engage another structure in such a manner to enable movement of the housing 62 relative to the structure in the direction of, for example, one of the length and width of the housing. In the illustrated embodiment, the rail 70 has a length that extends in the same direction as the length of the housing 62 and includes a body 72 extending from a face of the housing 62 in a plane perpendicular to a plane containing the face of the housing 62 and two arms 74, 76 extending in opposite directions from the body 72 at an angles to the plane containing the body 72. It should be understood that the shape of the rail 70 may vary and, further, that various structures other than a rail could be formed in or mounted to the housing 62 to enable a stationary or movable connection with another structure. Accordingly, the present disclosure is not intended to be limited to any particular rail or even any particular type of attachment element, but rather any suitable attachment element may be used.

Figure 10B:
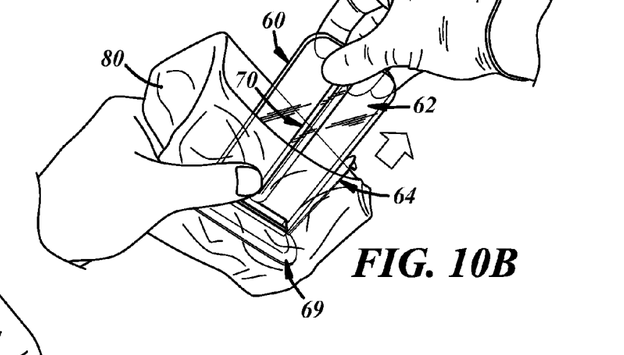

Referring now to FIGS. 10A-10G, a method for using an electronic device in a sterile medical environment in accordance with embodiments of the present teachings is shown. As shown in FIG. 10A, the method may begin with providing a sterile case such as case 60. Case 60 may be provided in a sealed bag 80 that is delivered to the sterile environment prior to or during a medical procedure. Referring to FIG. 10B, the method may continue with the step of removing the sterile case 60 from the bag 80. It will be understood that the sterile case 60 itself should be handled by individuals in the sterile environment using sterile gloves or other conventional means. Accordingly, while the bag 80 may be handled and opened by an individual having "unsterile" hands, the case 60 should be removed from the bag 80 by an individual having sterile hands (e.g., wearing sterile gloves). In an embodiment, this step may also comprise inserting the sleeve 69 of the case 60 (or at least a portion thereof) into the housing 62 once the case 60 is removed from the bag 80. In other embodiments, the sleeve 69 may be pre-installed in or with the housing 62 such that insertion of the sleeve into the housing 62 is not necessary.

Figure 10C:
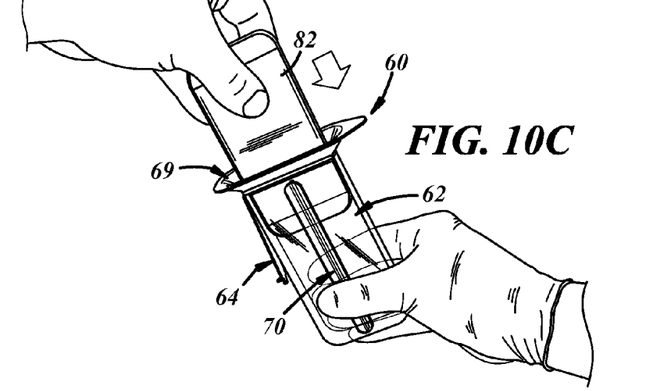

Referring to FIG. 10C, the method may continue with the step of inserting an electronic device 82 into the case 60. This step may include the substeps of inserting the device 82 through an opening in the housing 62 of the case 60 and inserting the device 82 through the sleeve 69 that is disposed partially within the housing 62 and extends outwardly therefrom through the opening in the housing 62. In an embodiment, this step may be performed by an individual with unsterile hands as the device being handled/inserted is also unsterile. Accordingly, an individual with sterile hands may hold case 60 and an individual with unsterile hands may insert the device 82 into the housing 62 of the case 60 via the sleeve 69. As discussed above, the sleeve 69 may taper moving in the direction distant from the housing 62 towards the housing 62 in order to guide the device 82 into the housing 62. The structure of the sleeve 69 prevents contact between the device 82 and a rim of the housing 62 surrounding the opening to thereby prevent biological contaminants on the device 82 from reaching exterior surfaces of the housing 62.

Figure 10D:
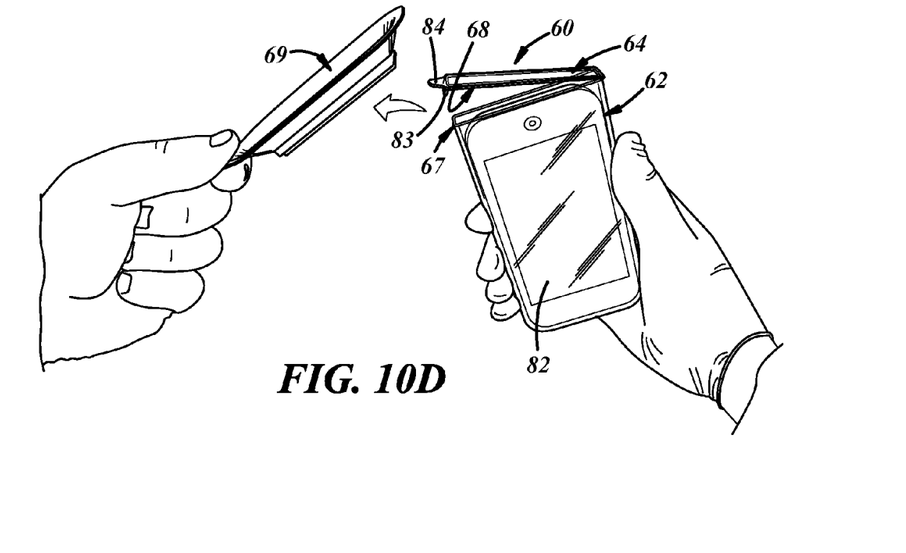

Referring to FIG. 10D, once the device 82 is fully inserted into the housing 62, the method may continue with the steps of removing the sleeve 69 from the housing 62 and moving the door 64 from an open position to a closed position. The sleeve 69 is removed from the housing by moving the sleeve 69 in a direction parallel to the length of the housing 62. Once the sleeve 69 is removed, the door 64 is rotated using the hinge 66 to close the opening in the housing 62. Seals 67, 68 on the door 64 and/or the rim of the housing 62 surrounding the opening act to prevent escape of any biological contaminants from the device 82 and the interior of housing 62 into the sterile environment. In an embodiment, a latch 83 may also be engaged so as to secure the door in a closed position. More particularly, in an embodiment, the housing 62 and the door 64 may include complementary latching elements that when coupled or engaged, serve to latch and secure the door in a closed position. Latch 83 may comprise any suitable latch known in the art as the present disclosure is not intended to be limited to any particular type of latch. Additionally to facilitate the closing (and opening of the door 64), in at least some embodiments the door 64 may further include a grip tab 84 that a user may grip when opening or closing the door 64. The grip tab 84 may extend perpendicularly to the longitudinal axis of the container (as shown in FIG. 9), or alternatively may extend parallel to the longitudinal axis or at some other suitable angle relative thereto.

Figure 10E:
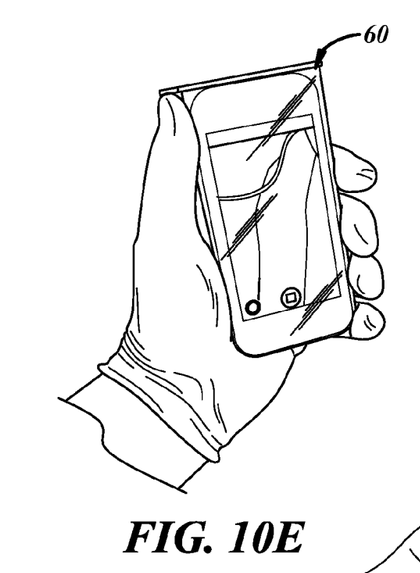
Figure 10F:
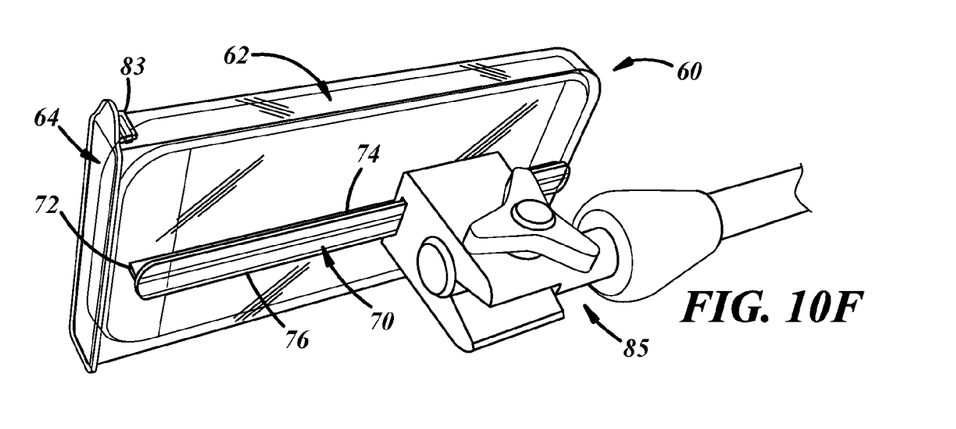

Referring to FIG. 10E, once the door 64 is closed, device 82 may be used in a conventional manner during a medical procedure. A flexible, transparent, electroconductive face of the housing 62 permits interaction with a touch screen display on the device 82. A transparent window on an opposite face permits use of a camera, flash, sensors, etc. on the device 82 to capture images of patient anatomy and the procedure. As shown in FIG. 10E, the sterile case 60 may be handled and held in place by a medical practitioner. Alternatively, as shown in FIG. 10F, the method may include the step of mounting the case 60 (with the enclosed device 82) onto a structure such as arm 85. As discussed above, in one embodiment, the housing 62 includes a rail 70 formed thereon and configured to engage a complementary receptacle in the arm 85 in order to mount the case 60 and allow the case 60 (and device 82) to be move in the direction of the length of the housing 62.

Figure 10G:
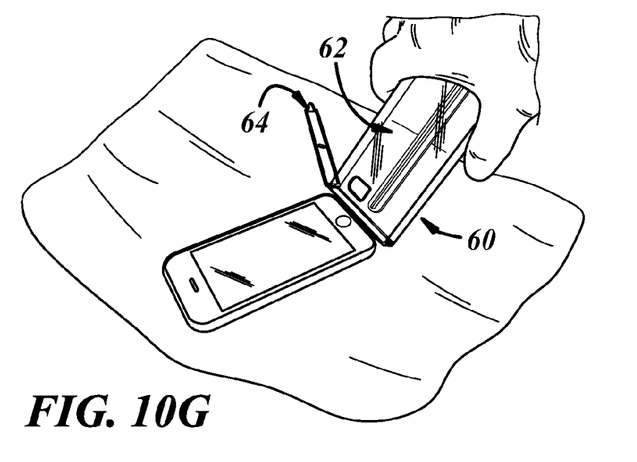

Referring to FIG. 10G, the method may conclude with removing the device 82 from the case 60 upon completion of the medical procedure. The device 82 is removed by moving the door 64 from the closed position to an open position such that the device 82 may be removed from the housing 62 through the opening in the housing 62.

An advantage of a sterile case in accordance with the present teachings is that it provides a means for using an electronic device, for example a (unsterile) general purpose electronic device, in a sterile medical environment, as well as provides a way of transferring an unsterile electronic device into a sterile case without compromising the sterility of the case. As a result, surgeons and other medical practitioners are able to realize the benefits of using such devices during medical procedures without increasing the risk of infection to patients.

While the invention has been shown and described with reference to one or more particular embodiments thereof, it will be understood by those of skill in the art that various changes and modifications can be made without departing from the spirit and scope of the invention.

As used in this specification and claims, the terms "e.g.," "for example," "for instance," "such as," and "like," and the verbs "comprising," "having," including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A sterile case for an electronic device, comprising:
a rigid housing having at least one face that is transparent and electroconductive and having an opening configured to permit movement of the device into and out of the housing, the housing defining a rim about the opening;
a door attached to the housing and configured to move between a closed position in which the door closes the opening in the housing and an open position in which the door is distant from the opening in the housing; and
a sleeve configured to be received, when the door is in the open position, partially within the housing and to extend outward from the housing through the opening, the sleeve defining a bore aligned with the opening and configured to receive the device and to permit and guide insertion of the device through the sleeve and into the housing without contact between the device and the rim of the housing.

2. The sterile case of claim 1, wherein the housing has a length and a width, and the opening of the housing is configured to permit movement of the device into and out of the housing in a direction parallel to one of the length and the width.

3. The sterile case of claim 2, wherein the opening is formed on a side of the housing defined by the width and a height of the housing such that the device moves into and out of the housing in the direction parallel to the length of the housing.

4. The sterile case of claim 1 further comprising a first seal formed on the rim of the housing or the door of the housing.

5. The sterile case of claim 4 further comprising a second seal formed on the other of the rim of the housing and the door of the housing and configured to engage the first seal when the door is in the closed position.

6. The sterile case of claim 1 further comprising a hinge attaching the door to the housing.

7. The sterile case of claim 6 further comprising a latch to secure the door in a closed position.

8. The sterile case of claim 1, wherein the at least one face comprises a first face of the housing and the housing includes a second face defining a transparent window configured for alignment with a camera lens of the device.

9. The sterile case of claim 1, wherein when the sleeve is disposed within the housing, the bore of the sleeve tapers inwardly moving in a direction furthest from the opening in the housing towards the opening in the housing.

10. The sterile case of claim 1, wherein the sleeve comprises a removable sleeve that may be inserted into and removed from the housing.

11. A sterile case for an electronic device, comprising:
a rigid housing having at least one face that is transparent and electroconductive and having an opening configured to permit movement of the device into and out of the housing, the housing defining a rim about the opening and an attachment element for attaching the housing to another structure;
a door attached to the housing and configured to move between a closed position in which the door closes the opening in the housing and an open position in which the door is distant from the opening in the housing; and
a sleeve configured to be received, when the door is in the open position, partially within the housing and to extend outward from the housing through the opening, the sleeve defining a bore aligned with the opening and configured to receive the device and to permit and guide insertion of the device through the sleeve and into the housing without contact between the device and the rim of the housing.

12. The sterile case of claim 11, wherein the attachment element comprises a rail formed on the exterior of the housing.

13. The sterile case of claim 11, wherein the at least one face of the housing is a first face of the housing and the attachment element is formed on a second face of the housing.

14. The sterile case of claim 11, wherein the attachment element enables movement of the housing in the direction of one of a length and a width of the housing relative to the structure while the housing is attached to the structure.

15. The sterile case of claim 11 further comprising a seal formed on the rim of the housing or the door of the housing.

16. The sterile case of claim 11, further comprising a hinge attaching the door to the housing, and a latch to secure the door in a closed position.

17. The sterile case of claim 11 wherein the at least one face comprises a first face of the housing and the housing includes a second face defining a transparent window configured for alignment with a camera lens of the device.

18. A sterile case for an electronic device, comprising:
a rigid housing having a length and a width, the housing having:
a first face that is transparent and electroconductive;
a second face defining a transparent window configured for alignment with a camera lens of the electronic device; and
an opening configured to permit movement of the device into and out of the housing in a direction parallel to one of the length and the width, the housing further defining a rim about the opening;
a door attached to the housing by a hinge and configured to move between a closed position in which the door closes the opening in the housing and an open position in which the door is distant from the opening in the housing;
a latch to secure the door to the housing when the door is in the closed position;
a sleeve configured to be received, when the door is in the open position, partially within the housing and to extend outward from the housing through the opening, the sleeve defining a bore aligned with the opening and configured to receive the device and to permit and guide insertion of the device through the sleeve and into the housing without contact between the device and the rim of the housing; and
a seal formed on the rim of the housing or the door of the case.

19. The sterile case of claim 6 wherein the hinge comprises a spring loaded hinge biasing the door to the closed position.

20. A sterile case for an electronic device, comprising:
a rigid housing having at least one face that is transparent and having an opening configured to permit movement of the device into and out of the housing, the housing defining a rim about the opening;
a door attached to the housing and configured to move between a closed position in which the door closes the opening in the housing and an open position in which the door is distant from the opening in the housing;
a sleeve configured to be received, when the door is in the open position, partially within the housing and to extend outward from the housing through the opening, the sleeve defining a bore aligned with the opening and configured to receive the device and to permit and guide insertion of the device through the sleeve and into the housing without contact between the device and the rim of the housing; and
a first seal formed on the rim of the housing and configured to engage a surface on the door of the housing when the door is in the closed position and a second seal formed on the door of the housing and configured to engage a surface of the housing when the door is in the closed position, wherein the first and second seals do not engage one another.

21. The sterile case of claim 1 wherein the sleeve includes a first portion configured to be received within the housing when the door is in the open position and a second portion configured to be located outside of the housing when the door is in the open position and configured to prevent insertion into the housing.

22. The sterile case of claim 21 wherein an external surface of the sleeve is configured to engage the rim of the housing.

23. A sterile case for an electronic device, comprising:
a rigid housing having at least one face that is transparent and having an opening configured to permit movement of the device into and out of the housing, the housing defining a rim about the opening;
a door attached to the housing and configured to move between a closed position in which the door closes the opening in the housing and an open position in which the door is distant from the opening in the housing; and, a sleeve configured to be received, when the door is in the open position, partially within the housing and to extend outward from the housing through the opening, the sleeve including a first portion configured to be received, when the door is in the open position, within the housing, and a second portion configured to be located, when the door is in the open position, outside of the housing and configured to prevent insertion into the housing, the first and second portions of the sleeve defining a shoulder configured to engage the rim of the housing such that an external surface of the sleeve is configured to engage the rim of the housing, and the sleeve defining a bore aligned with the opening and configured to receive the device and to permit and guide insertion of the device through the sleeve and into the housing without contact between the device and the rim of the housing.

24. The sterile case of claim 21 wherein the bore of the sleeve tapers inwardly within the second portion of the sleeve moving in a direction furthest from the opening in the housing towards the opening in the housing.

25. A sterile case for an electronic device, comprising:
a rigid housing having at least one face that is transparent and having an opening configured to permit movement of the device into and out of the housing, the housing defining a rim about the opening;
a door attached to the housing and configured to move between a closed position in which the door closes the opening in the housing and an open position in which the door is distant from the opening in the housing; and,
a sleeve configured to be received, when the door is in the open position, partially within the housing and to extend outward from the housing through the opening, the sleeve including a first portion configured to be received, when the door is in the open position, within the housing, and a second portion configured to be located, when the door is in the open position, outside of the housing and configured to prevent insertion into the housing, the sleeve defining a bore aligned with the opening and configured to receive the device and to permit and guide insertion of the device through the sleeve and into the housing without contact between the device and the rim of the housing, wherein the bore of the sleeve tapers inwardly within the second portion of the sleeve moving in a direction furthest from the opening in the housing towards the opening in the housing and does not taper within the first portion of the sleeve.

26. The sterile case of claim 21 wherein the first portion of the sleeve has an external surface with a shape that is complementary to a shape of an internal surface of the housing.

27. The sterile case of claim 26 wherein the external surface of the first portion of the sleeve is configured to engage the internal surface of the housing.

28. The sterile case of claim 20, wherein the at least one face of the housing is electroconductive.

29. The sterile case of claim 23, wherein the at least one face of the housing is electroconductive.

30. The sterile case of claim 23, further comprising a first seal formed on the rim of the housing and configured to engage a surface on the door of the housing when the door is in the closed position, and a second seal formed on the door of the housing and configured to engage a surface of the housing when the door is in the closed position, wherein the first and second seals do not engage one another.

31. The sterile case of claim 25, wherein the at least one face of the housing is electroconductive.

32. The sterile case of claim 25, further comprising a first seal formed on the rim of the housing and configured to engage a surface on the door of the housing when the door is in the closed position, and a second seal formed on the door of the housing and configured to engage a surface of the housing when the door is in the closed position, wherein the first and second seals do not engage one another.

33. The sterile case of claim 25, wherein the first and second portions of the sleeve define a shoulder configured to engage the rim of the housing.

* * * * *

UNITED STATES PATENT AND TRADEMARK OFFICE
CERTIFICATE OF CORRECTION

PATENT NO. : 9,642,429 B2
APPLICATION NO. : 14/854339
DATED : May 9, 2017
INVENTOR(S) : Robert L. Zondervan It is certified that error appears in the above-identified patent and that said Letters Patent is hereby corrected as shown below:

In the Claims

Column 9, Line 2, Claim 4, after "door of the" delete "housing" and insert --case--

Column 9, Line 5, Claim 5, after "door of the" delete "housing" and insert --case--

Column 9, Line 53, Claim 15, after "door of the" delete "housing" and insert --case--

Column 12, Line 22, Claim 30, after "door of the" delete "housing" and insert --case--

Column 12, Line 24, Claim 30, after "door of the" delete "housing" and insert --case--

Column 12, Line 31, Claim 32, after "door of the" delete "housing" and insert --case--

Column 12, Line 33, Claim 32, after "door of the" delete "housing" and insert --case--

Signed and Sealed this
Fourth Day of July, 2017

Joseph Matal
*Performing the Functions and Duties of the
Under Secretary of Commerce for Intellectual Property and
Director of the United States Patent and Trademark Office*